(12) United States Patent
Busch et al.

(10) Patent No.: US 7,911,608 B2
(45) Date of Patent: Mar. 22, 2011

(54) SPECTROSCOPIC DETERMINATION OF ENANTIOMERIC PURITY

(75) Inventors: Kenneth W. Busch, Waco, TX (US); Dennis H. Rabbe, Crawford, TX (US)

(73) Assignee: Baylor University, Waco, TX (US)

( * ) Notice: Subject to any disclaimer, the term of this patent is extended or adjusted under 35 U.S.C. 154(b) by 354 days.

(21) Appl. No.: 11/664,079

(22) PCT Filed: Sep. 30, 2005

(86) PCT No.: PCT/US2005/035481
§ 371 (c)(1), (2), (4) Date: Jun. 26, 2009

(87) PCT Pub. No.: WO2006/039648
PCT Pub. Date: Apr. 13, 2006

(65) Prior Publication Data
US 2009/0302207 A1    Dec. 10, 2009

Related U.S. Application Data

(60) Provisional application No. 60/615,123, filed on Oct. 1, 2004.

(51) Int. Cl.
*G01J 3/447*    (2006.01)

(52) U.S. Cl. ............................................. 356/327; 250/282
(58) Field of Classification Search .................. 356/300, 356/327; 250/282
See application file for complete search history.

(56) References Cited

U.S. PATENT DOCUMENTS 5,912,740 A * 6/1999 Zare et al. ..................... 356/437

* cited by examiner

*Primary Examiner* — Tarifur Chowdhury
*Assistant Examiner* — Abdullahi Nur
(74) *Attorney, Agent, or Firm* — Jackson Walker L.L.P.

(57) ABSTRACT

A new method and strategy for the quantitative determination of enantiomeric purity that combines polarimetry, spectroscopy, and chemometric modeling. Spectral data is collected after a light beam is passed through a first polarimeter, a sample of a chiral compound, and a second polarimeter oriented at a 45 degree angle relative to the first polarimeter. The spectral data for samples of known enantiomeric composition is subjected to a type of multivariate regression modeling known as partial least squares ("PLS-1") regression. The PLS-1 regression produces a mathematical model that can be used to predict the enantiomeric composition of a set of samples of unknown enantiomeric purity.

4 Claims, 20 Drawing Sheets

SPECTROSCOPIC DETERMINATION OF ENANTIOMERIC PURITY

This application claims priority to U.S. Provisional Patent Application Ser. No. 60/615,123, entitled "Spectroscopic Determination of Enantiomeric Purity" filed on Oct. 1, 2004, the entire content of which is hereby incorporated by reference.

BACKGROUND

This invention relates to methods and strategies for determining the enantiomeric purity of chiral compounds through the use of the optical activity of enantiomers, spectroscopy, polarimetry, and chemometric modeling.

Chiral molecules are molecules that are isomers that are mirror images and yet cannot be superimposed on each other. They are enantiomers. The enantiomers differ from achiral compounds in that enantiomers have no plane of symmetry. The general rule is any structure that doesn't have a plane of symmetry is chiral, and any structure that has a plane of symmetry cannot exist as two enantiomers.

On the molecular level, if a molecule contains a carbon atom that is bound to four different groups or atoms it will not have a plane of symmetry and must be chiral. Such a carbon atom is said to be a stereogenic or chiral center. Other formations such as a helix can be chiral, also. A chiral compound in either form can be separated or synthesized to its pure state. A mixture of 50% of each of the enantiomers is a racemate.

Another property of enantiomers or chiral compounds is the fact that they are capable of rotating the plane of oscillation of a linearly polarized light beam upon passage through a medium in either crystalline, liquid, or solution form. The amount of rotation is proportional to the percent composition of each enantiomer. Therefore a racemate mixture or 50%-50% mixture is optically inactive because each type of enantiomer cancels out the other's effect on the rotation of the polarized light. In contrast, one form will rotate the light the maximum possible in one direction while the other enantiomerically pure form will rotate the light in the opposite direction the same maximum value.

Enantiomers can be classified as R and S, but can also be identified by the direction of which way they rotate light. If the compound rotates the light to the right, the convention says that the enantiomer is (+) or dextrotary. If the compound rotates the light to the left, then this enantiomer is designated as (−) or laevorotatory.

Many biological systems are configured chirally. The difference between two enantiomers can have enormous consequences because many important biological molecules are chiral. Amino acids are the building blocks of proteins and enzymes in all terrestrial life and have the formula $^+H_3NCH(R)CO_2^-$. Note that the C atom is bonded to four different groups, making it a chiral center. All naturally occurring amino acids exist as only one of the two possible enantiomers, meaning that all proteins and enzymes are also chiral. Sugars, polysaccharides and peptides are also chiral.

Drug activity results from pharmacological and pharmokinetic processes by which it enters, interacts with, and leaves the body. Many examples exist in which enantiomers show marked differences in their bioavailability, distribution, metabolic, and permeability behavior in which stereochemical parameters determine the fundamental action of the compound on the biochemical systems of a living organism. For instance, the β-blocker propranol or the cardotonic agent verapamil have different efficacy when administered as racemates and not as the active enantiomer. The R form of PROZAC is the active configuration of the drug while the S form is inactive. In the late fifties and early sixties, the racemate of the drug Thalidomide was given to pregnant women to control nausea and as a sedative. The R configuration was responsible for desired effect; however, unknown to the medical community, the S form was later found to be a teratogen. A teratogen is a chemical that causes developmental defects in unborn infants. This drug was responsible for hundreds of thousands of birth defects before this fact was discovered.

Economic and safety interests are obvious and are paramount in the development of new chiral substances and technological advances. Single-enantiomer sales have shown a steady annual increase. Consequently, many of the top selling drugs are marketed as single enantiomer compounds.

The need for improved strategies for the assessment of enantiomeric purity arises from increased pressure on the pharmaceutical industry by government agencies for documentation on the pharmacological effects of individual enantiomers and the simultaneous demand in drug development for determination of enantiomeric excess in large combinatorial libraries. The significance of chirality on almost any pharmacological process is well documented. Also, economically, chiral technologies in other fields such as agrochemicals, food additives, fragrances, new materials and catalysts have come to the forefront. In conjunction with an ever increasing demand for enantiomerically pure compounds efficient strategies for analysis and preparation of chiral molecules are required. For high throughput screening strategies, slow chromatographic methods are not attractive. Rapid spectroscopic techniques are the most desirable.

Several methods are presently used to determine enantiomeric purity. The traditional and most commonly known is polarimetry. As mentioned earlier, the plane of oscillation of linearly polarized light is rotated in proportion to the enantiomeric make-up of a mixture of R and S enantiomers. Optical activity is observed and measured by means of an instrument known as a polarimeter, which was first used as a chemical instrument in about 1816. Light from a monochromic light source is passed through a polarizer, which linearly polarizes the light. It is then allowed to pass through a sample tube which contains the sample to be analyzed and then through a second polarizer. The angle of rotation is determined by maximizing the light passing through the second polarizer. This position would coincide with the plane of oscillation of the polarized light which would correlate with the angle of rotation. The polarimeter can be used to determine if a given substance is chiral or achiral by observing if it rotates light. The enantiomeric composition of chiral samples can be ascertained either quantitatively or qualitatively, since the rotation is correlated with the enantiomeric purity or composition. It can also be used to investigate equilibrium systems and reaction mechanisms. It is popular since it is a reliable, relatively simple, and well established technique. The disadvantage of polarimeter is that it is not very sensitive and is affected by chiral impurities.

Another strategy is the covalent synthesis and detection of diastereomers using enantiomerically pure derivatizing agents. In this scenario, the enantiomers are derivatized and then, since diastereomers have different chemical and physical properties, the enantiomeric purity can be detected using several techniques which include nuclear magnetic resonance spectroscopy.

Other classical methods of enantiomeric purity include the detection of transient diastereomeric interactions by NMR using chiral shift reagents, and the use of chiral stationary phases in chromatography. The last technology at present is the most desirable technique in terms of speed, accuracy, and adaptability of the ones mentioned.

Multivariate regression modeling ("MRM") is widely used in chemistry as a means of correlating spectral data with known compositional changes.

SUMMARY

This invention relates to new strategies for the quantitative determination of enantiomeric purity. The strategies combines optical activity of enantiomers, polarimetry, spectroscopy, and chemometric modeling.

Broadly, a first method for determining enantiomeric purity involves measuring the spectra of chiral compounds with a spectrometer. The spectra of a set of enantiomers may exhibit varying degrees of differences between the R and S forms. In particular, the spectra of the two enantiomeric forms exhibit slightly different band envelope shape. The maximum peak value appears to be the same, but the shape of the peak varies. This is completely against traditional convention since the physical properties of enantiomers should be the same, and, consequentially, the spectrum of each pure form should be the same.

Without wanting to be bound by theory, parity nonconserving effects due to neutral weak interactions could account for minor differences in the spectrum of enantiomers. Another possibility is conformational differences in the enantiomers when they are dissolved. The spectrum of a compound in solution is the summation of the spectra of many different conformations of all of the molecules. If the probability of the makeup of the conformations for each enantiomer differed slightly, the maximum of the absorption band would be in all likelihood the same, but the shape of the envelope of the band would be different. Solvent self interactions could also be a possibility. As the composition of the enantiomers varies, when one is much higher than the other, chiral solvent-like interactions should occur. This phenomenon has been documented for NMR and other techniques. The last is the influence of impurities in the samples. If the enantiomers had different impurities in the R and S forms, it is possible for the impurities to act as markers for each enantiomer and the statistical software would be able to predict because of them. Nevertheless, for whatever reason, there is enough variation in the spectra between the enantiomeric forms to enable calculating models that can accurately predict the enantiomeric composition of validation samples sets.

An additional method for determining enantiomeric purity involves the use of a light source, a first polarizer, a sample of a chiral compound, a second polarizer, and a spectrometer. FIG. 1 shows a general schematic diagram of an instrumental arrangement which can be used. An important aspect of this instrumental setup is the orientation of the plane of polarization of the polarizers relative to each other. The plane of polarization of the second polarizer is rotated such that it is oriented forty five degrees relative to the first. If a beam of light is polarized by the first polarizer and it passes through a sample that is not optically active (the racemate), the plane of oscillation of the electric fields of the light beam will not change. When the beam reaches the second polarizer, only approximately fifty percent of the light will pass through the second polarizer because it is oriented at a forty-five degree angle in relation to the first polarizer.

If the sample has a counter-clockwise optical rotation, based on its chirality, the light beam is rotated such that the plane of oscillation is oriented to be less parallel to the orientation of the second polarizer. This results in a decreased amount of light passing through the second polarizer. The spectrometer will record an apparent absorption, or more properly, a positive baseline shift. On the other hand, if the sample rotates the plane of oscillation in a clockwise direction, the plane of oscillation is oriented to be more parallel with the second polarizer. This results in increased light passing through the polarizer and a negative baseline shift recorded by the spectrometer. Since the optical rotation of a mixture of R and S enantiomers of a compound is proportional to the amount and direction of rotation, with a set of spectra in which the enantiomeric purity varies from 0 R-1 S φ to 1 R-0 S φ, a predictive model can be made to predict the enantiomeric composition of an mixture of unknown enantiomeric purity. Because the spectral data recorded by the spectrometer is not traditional absorption spectral data, but rather apparent changes in absorption due to the optical rotation of light, it may be referred to as "pseudo-absorption" spectral data.

Compared with traditional polarimetry, the present invention offers several advantages. Perhaps the most significant advantage is the absence of moving parts. In traditional polarimetry, the second polarizer is rotated to maximize the intensity of the light passing through the instrument. The optical activity of a sample is measured by determining the angle through which the second polarizer must be rotated to maximize the intensity of the light passing through the instrument. It is difficult to determine the angle that gives the maximum intensity. In the current method, the polarizers are maintained in a fixed orientation and the light intensity transmitted by the device is analyzed as a function of wavelength by means of chemometrics. Most polarimeters make measurements only at a single wavelength. In the present invention, a wide range of wavelengths is used, like that in optical rotatory dispersion. In this case, however, what is being measured is the apparent change in absorbance induced by the rotation caused by the sample in relation to the fixed orientation of the second polarizer, rather than the actual optical rotation. Since optical rotation varies strongly with wavelength, use of a range of wavelengths can increase the specificity of the technique. Moreover, using a range of wavelengths permits the use of powerful data treatment strategies like multivariate regression modeling, which can focus in on a desired correlation in the presence of other sources of variation (like noise). Another advantage is speed. Once the regression model has been made, data on unknown samples can be obtained rapidly because no polarizer rotation is required. Finally, because small differences in absorbance are readily determined, this instrument can be used with smaller cells of 20 mm pathlength. Typical cells used in polarimeters are 10 to 20 cm long. Use of smaller cells reduces the amount of sample needed.

A type of multivariate regression modeling known as partial least squares ("PLS-1") regression can be used to develop a mathematical model that is used to predict the enantiomeric composition of a set of samples based on spectral data.

Multivariate regression is widely known in many areas of chemistry and can serve as a particularly powerful computational tool for correlating spectral data with known compositional changes in a test set of samples. The basic objective of the method is to develop a mathematical model that relates two sets of variables to each other so that the independent or X-variables can be used to predict the dependent or Y-variable. In this case, the X-variables are the spectral information and the Y-variable is the enantiomeric composition.

To avoid problems with colinearity in the data, all multivariate regression techniques require an orthogonal basis set or coordinate system on which to represent the data. To achieve this condition, modern regression techniques employ projection methods to obtain a series of variance-scaled eigenvectors that can serve as a new coordinate system for the data. This form of data decomposition assures an orthogonal coordinate system for the data. At the same time, it provides a way to reduce the dimensionality of the data because only the major eigenvectors are needed to represent the data. Finally, when the data are represented on the new coordinate system, new insight is often gained as new relationships that were formerly obscured in the old coordinate system are revealed.

Broadly, one aspect of the present invention involves a method for determining an unknown enantiomeric composition of a chiral compound in an unknown sample, comprising the steps of:

(1) preparing a series of known samples, each of the known samples comprising a chiral compound having a known enantiomeric composition, wherein in each of the known samples, the enantiomeric composition of the chiral compound is varied;

(2) collecting absorption spectral data of the known samples at various wavelengths;

(3) performing a principal component analysis to select a spectral range of wavelengths in which the spectral differences arising in each of the known samples due to an influence of the enantiomeric composition is most appreciable to give the selected range of wavelengths;

(4) performing a partial-least-squares regression of the spectral data over the selected range of wavelengths for each of the series of the known samples to determine a series of regression coefficients;

(5) entering the series of regression coefficients for the selected range of wavelengths into a regression vector;

(6) collecting absorption spectral data of an unknown sample at various wavelengths to give unknown spectral data, wherein the unknown sample comprises the chiral compound of the known samples; and (7) inserting the unknown spectral data into the regression vector to allow calculation of the unknown enantiomeric composition of the chiral compound in the unknown sample.

Another aspect of the present invention involves a method for determining an unknown enantiomeric composition of a chiral compound in an unknown sample using polarimetry, comprising the steps of:

(1) preparing a series of known samples, each of the known samples comprising a chiral compound having a known enantiomeric composition, wherein in each of the known samples, the enantiomeric composition of the chiral compound is varied;

(2) collecting "pseudo-absorption" spectral data of the known samples by passing light of various wavelengths through a first polarizer, the known sample, and a second polarizer oriented at a 45 degree angle with respect to the first polarizer, and recording the resultant light intensity with a spectrometer;

(3) performing a principal component analysis to select a spectral range of wavelengths in which the spectral differences arising in each of the known samples due to an influence of the enantiomeric composition is most appreciable to give the selected range of wavelengths;

(4) performing a partial-least-squares regression of the spectral data over the selected range of wavelengths for each of the series of the known samples to determine a series of regression coefficients;

(5) entering the series of regression coefficients for the selected range of wavelengths into a regression vector;

(6) collecting "pseudo-absorption" spectral data of an unknown sample at various wavelengths to give unknown spectral data, wherein the unknown sample comprises the chiral compound of the known samples; and (7) inserting the unknown spectral data into the regression vector to allow calculation of the unknown enantiomeric composition of the chiral compound in the unknown sample.

DETAILED DESCRIPTION OF PREFERRED EMBODIMENTS

Figure 1:
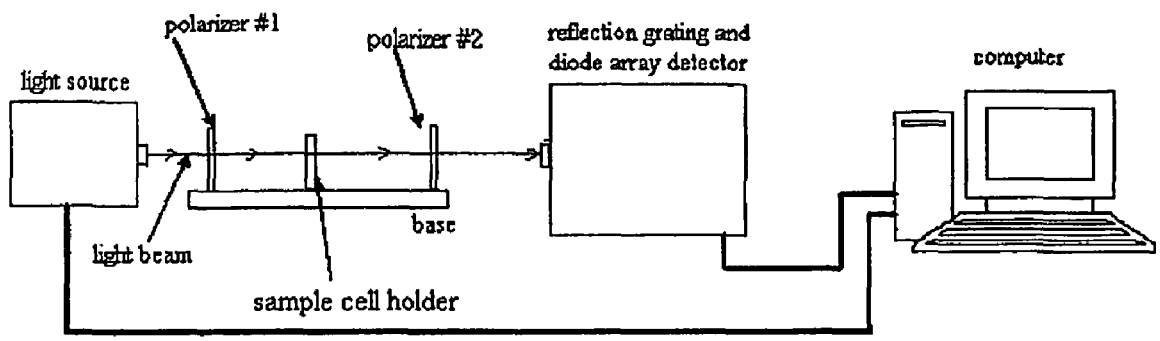
FIG. 1 shows a general schematic diagram of an instrumental arrangement which can be used in accordance with the claimed method.

The current invention pertains to methods for determining enantiomeric purity of solutions of compounds whose enantiomeric composition is unknown. The methods involve optical activity of enantiomers, spectroscopy, polarimetry, and chemometric modeling. A type of multivariate regression modeling known as partial least squares ("PLS-1") regression is used to develop a mathematical model that can be used to predict the enantiomeric composition of a set of samples.

Multivariate modeling of the spectral data is a two-step procedure. In the first or calibration phase, a mathematical model in the form of a regression vector is determined with a training set of samples whose Y-variable is known. In particular, PLS-1 regression is used to construct a linear predictive model for enantiomeric compositions based on the spectral data. The equation below shows the typical format of a regression vector.

$$X_R = k_0 + k_1 A_1 + k_2 A_2 + \ldots + k_n A_n$$

In this equation, $X_R$ is the unknown mol fraction of guest molecule in the sample, $k_i$ are the coefficients of the regression vector, and $A_i$ are the absorbances at the different i wavelengths (i=1, ..., n) for a given unknown sample. The variable $k_0$ is a constant regression coefficient. The regression coefficients ($k_i$) and the regression constant ($k_0$) are calculated using the PLS-1 regression algorithm, which may preferably be performed on a computer system utilizing suitable software (Unscrambler®, CAMO, Oslo, Norway).

The PLS-1 algorithm is especially powerful as a means of regression because both the X- and the Y-data are actively involved in the construction of the new basis set made up of PLS components. In this way, the PLS regression algorithm focuses on those aspects of the data that are most important in predicting Y. Partial least-squares regression has a goal of minimizing sample response prediction error by seeking linear functions of the predictors that explain as much variation in each response as possible, as well as accounting for variation in the predictors. The techniques implemented in the PLS-1 procedure work by extracting successive linear combinations of the predictors. In particular, the PLS-1 method balances the two objectives, seeking factors that explain both response and predictor variation.

In the second or validation phase of multivariate modeling, the mathematical model developed for the training set of samples is used to predict the enantiomeric composition of another independently obtained set of samples whose enantiomeric composition is also known. Here, the spectral data for the validation set of samples are obtained, and the equation above is used to predict the enantiomeric composition of the samples in the set from the measured spectral data. In this phase, the values of the Y-data predicted by the model are compared with the known values for the validation set.

In particular, the methods for determining the enantiomeric composition of an unknown sample of a chiral compound involve the following steps. First, a series of samples is prepared using a chiral compound. Each sample has a known enantiomeric composition which ranges from 0 R-1 S $\phi$ to 1 R-0 S $\phi$.

Second, spectral data are collected for each sample at various wavelengths. The spectral data may be collected directly from the samples, if the chiral compound demonstrates sufficient spectral differences between the R and S configurations. Some examples of compounds which show spectral differences between their configurations include limonene, 2-octanol, pulegone, leucinol, 1,2-propanediol, α-methylbenzyl amine, N-benzyl-α-methylbenzylamine, 1-phenylethyl isocyanate, and menthyl acetate. A preferred spectrometer for measuring the spectral data is manufactured by Hewlett Packard, Model 8453 (Palo Alto, Calif.). The preferred spectrometer is a dispersive spectrometer utilizing two light sources and a photodiode array detector that enables the system to obtain a spectrum covering the wavelength range from 190 to 1100 nm. The spectra of the samples are then taken using UV quartz cells with a path length of 2 mm.

Alternatively, the spectral data is collected by a spectrometer after a beam of light is passed through a first polarizer, the known sample, and a second polarizer oriented at a 45 degree angle relative to the first polarizer. Preferred polarizers that can be used are of the Glan-Thompson type, constructed using $CaCO_3$ crystals (Oriel Co. part number 25706, Stafford, Conn.). To use the method involving polarimetry, the system must be modified in order to accommodate the type of spectral data used in the current method. In particular, a base must be installed in the instrument. As shown in FIG. 1, the base is oriented between the light source and the dispersive element, which in this spectrometer is a reflection grating. The base replaces the standard sample cell holder and is designed to hold two polarizers on either side of the sample holder. After installation of the base, a light beam can pass through the first polarizer, the sample cell holder, and the second polarizer in succession before it reaches the reflection grating and diode array detector.

Once the spectral data are collected by either method, the analysis is the same. In the third general step, principal component analysis is used to select a spectral range in which the spectral differences that arise in each sample due to the influence of the enantiomeric composition on the optical rotation of light are most appreciable. Fourth, PLS-1 regression of the spectral data for the selected wavelength range is performed for the data collected for each of the samples to determine the regression coefficients at each wavelength. Fifth, the calculated series of regression coefficients is entered into the regression vector.

Finally, a sample of the unknown compound is prepared. The unknown compound is the same compound used to prepare the series of samples, but its enantiomeric composition is unknown. Spectral data for the unknown sample are collected at each wavelength in the selected range of wavelengths. If the method using polarimeters was used to collect the spectral data for the calculation of the regression vector, then the spectral data of the unknown sample should be measured in the same manner. The spectral data for the unknown sample is then inserted into the regression vector, allowing the calculation of the enantiomeric composition.

The regression vector is represented by the following formula:

$$X_R = k_0 + k_1 A_1 + k_2 A_2 + \ldots + k_n A_n$$

wherein $X_R$ is the unknown enantiomeric composition of the chiral compound in the unknown sample, $k_i$ is the series of regression coefficients calculated for the selected range of wavelengths, $A_i$ is the absorption spectral data of the unknown compound for the selected range of wavelengths, i is the selected range of wavelengths, 1-n, and $k_0$ is the constant regression coefficient. Thus, the regression coefficient at each wavelength is multiplied by the absorbance of the unknown sample measured at the same wavelength, to give a number represented as $k_i A_i$. This is done for each wavelength within the selected wavelength range. These numbers, along with the constant regression coefficient $k_0$, are then added together to give the enantiomeric composition of the unknown sample ($X_R$).

This strategy is useful for determining the enantiomeric compositions of various chiral compounds. Any chiral compound that is capable of rotating the plane of oscillation of a linearly polarized light beam can be used.

Example 1

Generation and Evaluation of Regression Model for Pulegone

Figure 2:
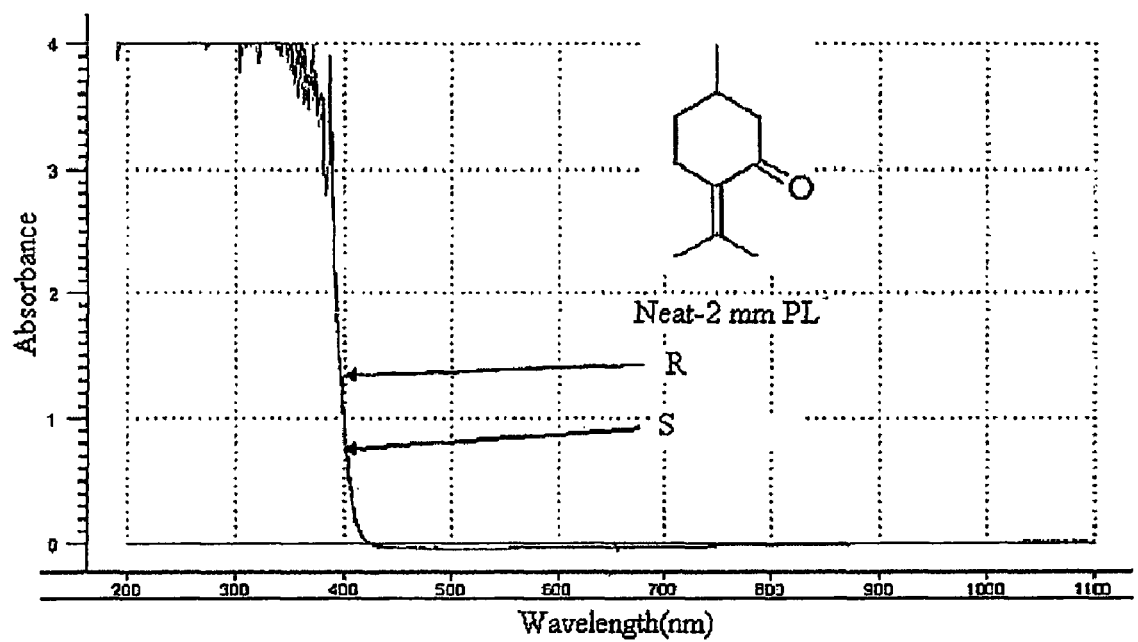
FIG. 2 shows the spectrum of pulegone taken neat using a 2 mm UV quartz cell.
Figure 3:
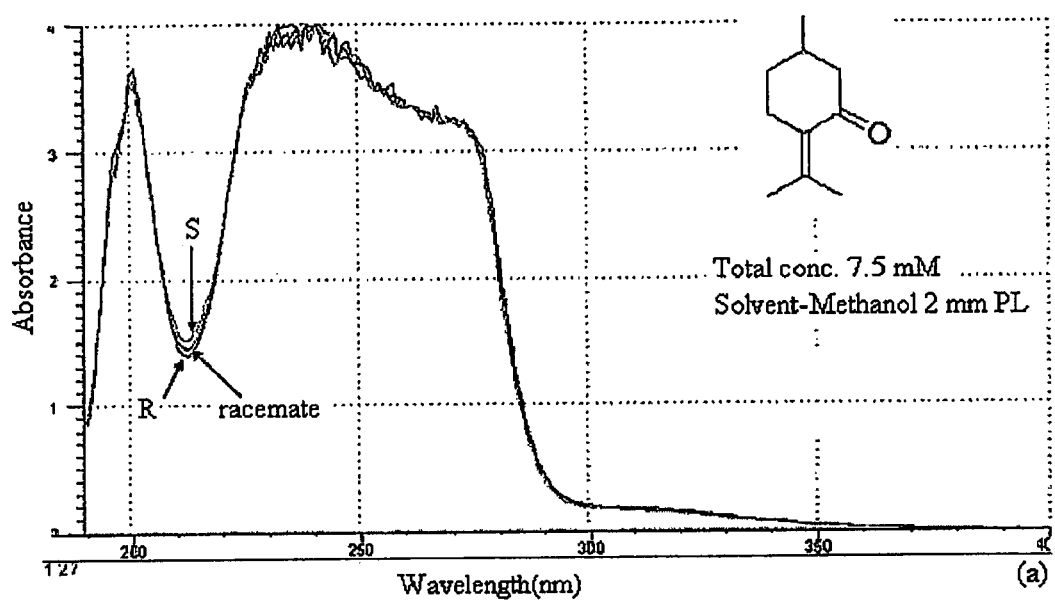
FIG. 3 shows the spectra of pulegone enantiomeric mixtures showing differences in the UV spectral envelope over a full range of wavelengths.
Figure 4:
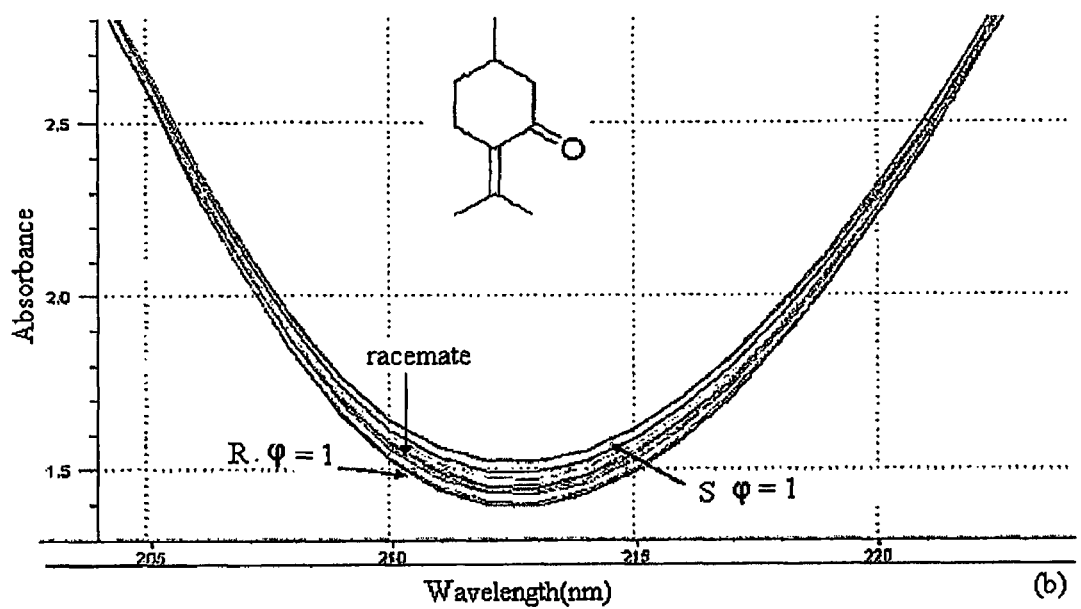
FIG. 4 shows the spectra of pulegone enantiomeric mixtures showing differences in the UV spectral envelope over an enhanced wavelength scale.

The spectra of the R and S configurations of pulegone, taken neat with a path length of 2 mm, showed no apparent difference in the two spectra, as shown in FIG. 2. FIG. 2 also shows the structure of pulegone. This was the only enantiomeric pair in which this was the case. In all the other spectra, small differences were apparent even without dilution. As shown in FIG. 3, which also shows the structure of pulegone, when methanol solutions 7.5 mM in each enantiomer were prepared and the spectra were taken, small differences in the spectra became apparent. FIG. 4 shows ten spectra of pulegone taken of methanol solutions with constant total concentrations, but varying the mixture composition from 0 to 1 φ in each conformation. The differences become more discernable when plotted in this manner, over a more limited range of wavelengths.

Solutions using methanol as the solvent were made for a calibration set using accepted volumetric techniques. The calibration set consisted of mixtures with mole fractions ranging from 0 R-1 S to 1 R-0 S with the total concentration being held at a constant 15 mM (except for pulegone which was done at 7.5 mM). A separately prepared validation set was also independently made consisting of five mixtures randomly chosen from low to high ratios in order to test the predictive performance of the model. CAMO's Unscrambler® software was used to calculate the models and the predictions.

Figure 5:
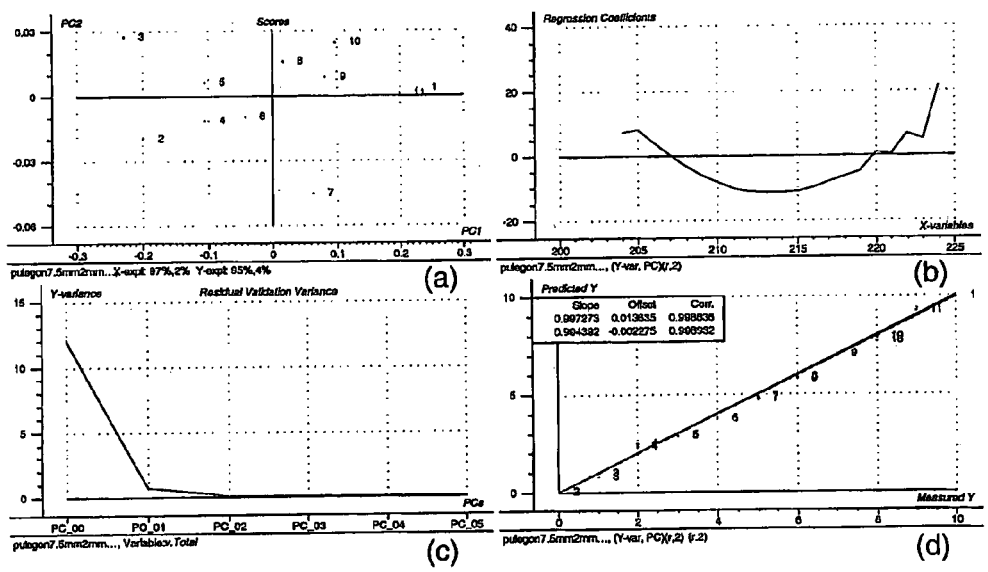
FIG. 5 shows the PLS1 regression model for R-pulegone solutions over a wavelength range of 205-225 nm: (a) Scores plot of the first principal component ("PC1") versus the second principal component ("PC2"); (b) Plot of the regression coefficients as a function of wavelength; (c) Residual variance as a function of the number of principal components; and (d) Plot of the concentration of R limonene predicted by the model versus the known value.

The statistical results for pulegone can be seen in FIG. 5. The scores plot shows an even distribution of the samples. The residual validation variance plot in FIG. 5(c) indicates that two principal components explain 99 percent of both the x and y data. In the predicted vs. measured plot in FIG. 5(d), the correlation coefficient is 0.9986 and the validation coefficient is 0.997, which indicates a very high degree of correlation. A PLS 1 model was calculated for the S form also. The major difference was seen in the regression coefficient plot, where the S and R forms were basically mirror image plots of each other. Table 1 below gives the numerical results for the prediction set for the R and S enantiomeric forms of pulegone, with values reported as mole fractions. The percent error for the R form was 11.44 while the percent error for the S form was 7.

TABLE 1

Numerical results for the prediction sets of pulegone R and S enantiomers

| Sample | Predicted φ | Reference φ | Error | Abs. Error | % Error |
|---|---|---|---|---|---|
| Pulegone-R λ range 205-225 | | | | | |
| 1 | 0.993 | 0.922 | 0.071 | 0.071 | 8 |
| 2 | 0.296 | 0.345 | −0.049 | 0.049 | 14 |
| 3 | 0.6 | 0.638 | −0.038 | 0.038 | 6 |
| 4 | 0.191 | 0.162 | 0.029 | 0.029 | 18 |
| | | | avg. | 0.047 | 11 |
| Pulegone-S λ range 205-225, 275-390 | | | | | |
| 1 | 0.943 | 0.922 | 0.021 | 0.021 | 2 |
| 2 | 0.385 | 0.345 | 0.04 | 0.040 | 12 |
| 3 | 0.612 | 0.638 | −0.026 | 0.026 | −4 |
| 4 | 0.178 | 0.162 | 0.016 | 0.016 | 10 |
| | | | avg | 0.026 | 7 |

Example 2

Generation and Evaluation of Regression Model for N-Benzyl-A-Methylbenzylamine

Figure 6:
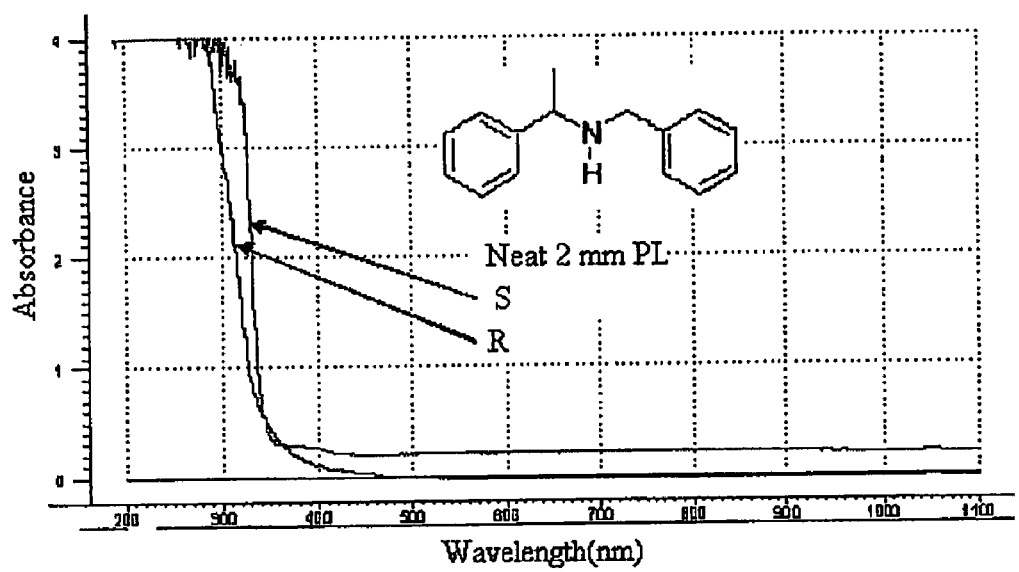
FIG. 6 shows the spectra of R and S N-benzyl-α-methylbenzylamine taken in a quartz cell with a path length of 2 mm.
Figure 7:
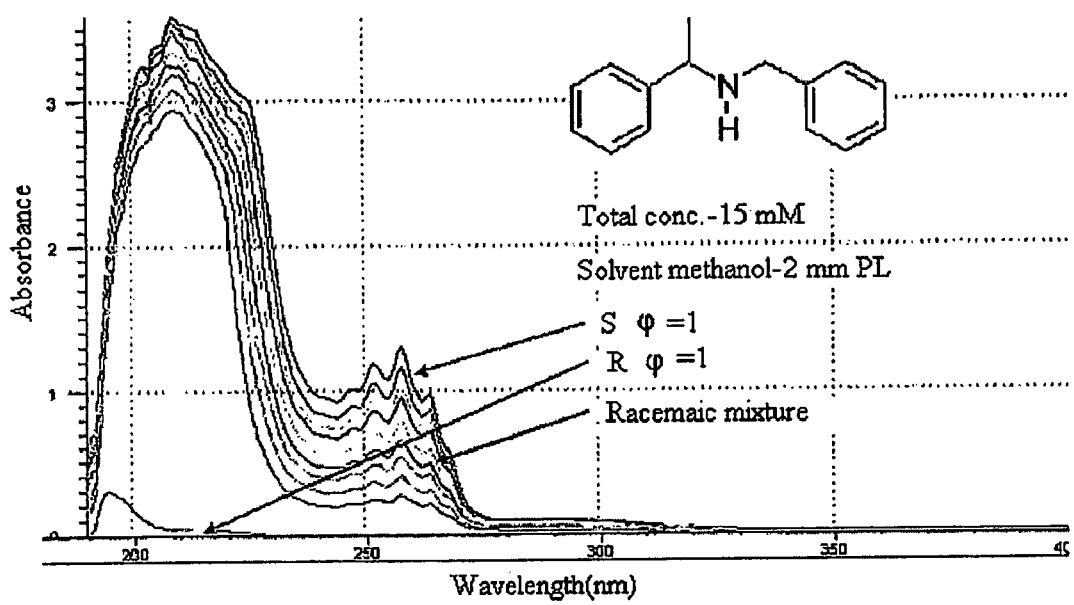
FIG. 7 shows ten spectra of R and S N-benzyl-α-methylbenzylamine mixtures dissolved in methanol with a constant total concentration of 15 mM.

FIG. 6, which shows the spectra of the R and S forms of N-benzyl-α-methylbenzylamine overlaid on the same plot, shows that even though the absorbances of the two go off scale below 300 nm, small differences in the spectra are apparent. The spectra of the calibration set can be seen in FIG. 7. The spectral differences for this compound are quite obvious when solvated. As described in the previous section, the solutions with methanol as the solvent were made using accepted volumetric methods with the mole fraction of each enantiomer varying from 0 R-1 S to 1 R-0 S. The total concentration of the two enantiomers was maintained constant at 15 mM. The spectra of the solutions were taken using a 2 mm path length quartz cell.

Figure 8:
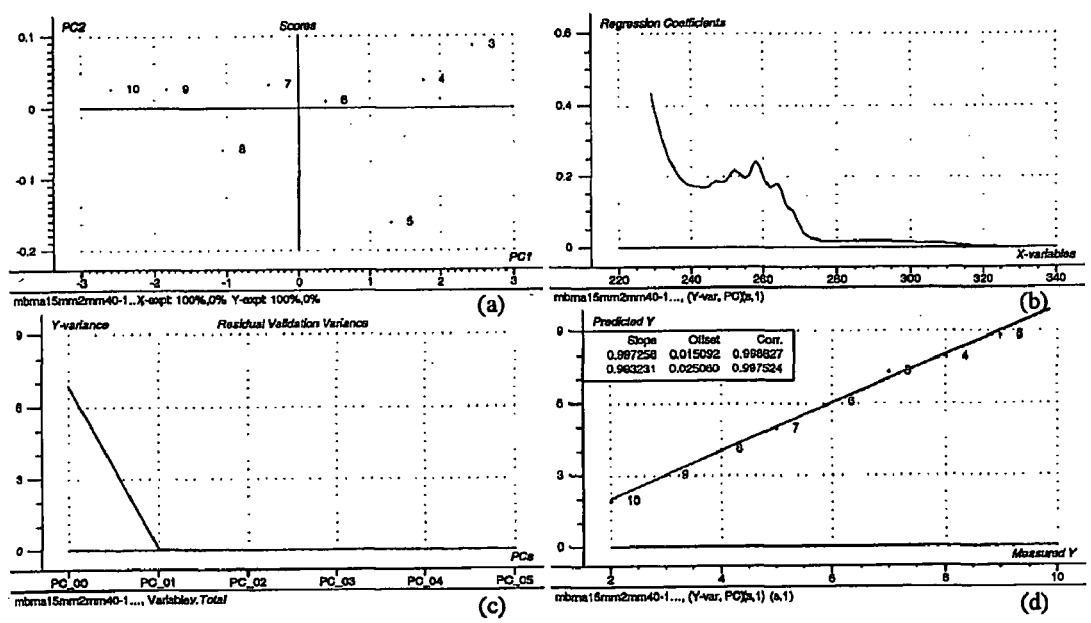
FIG. 8 shows the PLS1 regression model for (S)N-benzyl-α-methylbenzylamine solutions over a wavelength range of 230-330 nm: (a) Scores plot of the first principal component ("PC1") versus the second principal component ("PC2"); (b) Plot of the regression coefficients as a function of wavelength; (c) Residual variance as a function of the number of principal components; and (d) Plot of the concentration of (S)N-benzyl-α-methylbenzylamine predicted by the model versus the known value.
Figure 9:
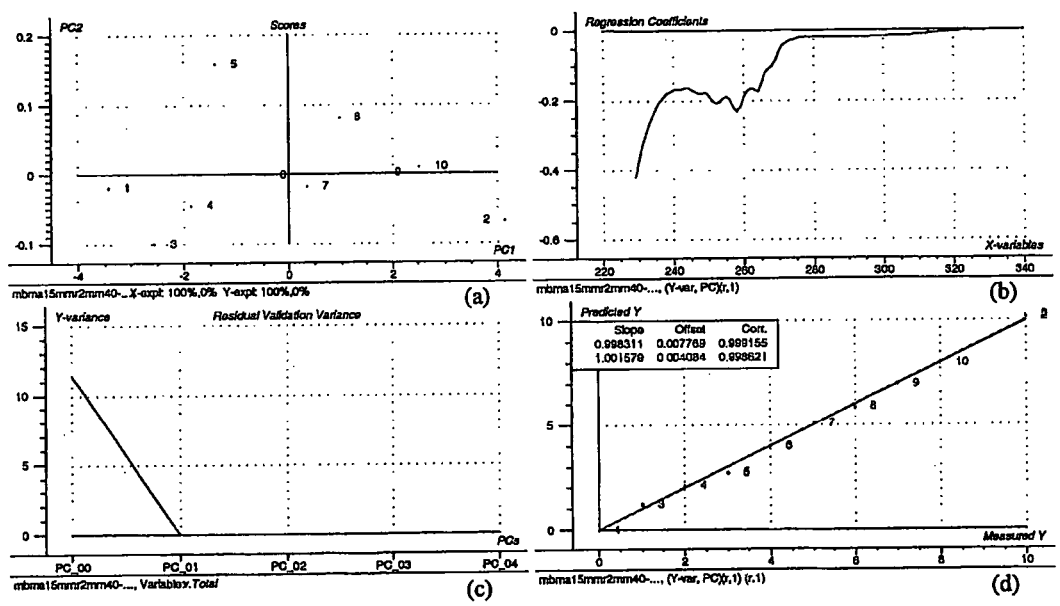
FIG. 9 shows the PLS1 regression model for (R)N-benzyl-α-methylbenzylamine solutions over a wavelength range of 230-330 nm: (a) Scores plot of the first principal component ("PC1") versus the second principal component ("PC2"); (b) Plot of the regression coefficients as a function of wavelength; (c) Residual variance as a function of the number of principal components; and (d) Plot of the concentration of (R)N-benzyl-α-methylbenzylamine predicted by the model versus the known value.

The Unscrambler® software was used to calculate regression models for both the R and S forms of the enantiomer using the spectral data and the results are presented in FIG. 8 for the S form and FIG. 9 for the R form. The model was calculated over the spectral range of 230-330 nm. Several ranges were tried, but this gave the best results. It is an interesting note that the results of the two models as seen in FIGS. 8 and 9 are very similar except for the regression coefficient plots in frames 8(*b*) and 9(*b*) which are mirror images of each other. The correlation and validation coefficients for both models are greater than 0.99 and one principal component explains 100 percent of the x and y variance. The results for the prediction set are given in Table 2, with values reported as mole fractions. For the S enantiomer the average relative error was 4 while the average relative error for the R enantiomer was 9.

TABLE 2

Numerical results for prediction of the validation samples

| Sample | Prediction φ | Reference φ | Error | Abs. Error | % Error |
|---|---|---|---|---|---|
| N-Benzyl-α-methylbenzylamine-S ||||||
| 1 | 0.631 | 0.612 | 0.019 | 0.019 | 3.1 |
| 2 | 0.153 | 0.165 | −0.012 | 0.012 | 7.3 |
| 3 | 0.694 | 0.706 | −0.012 | 0.012 | 1.7 |
| 4 | 0.904 | 0.868 | 0.036 | 0.036 | 4.1 |
|  |  |  | Avg. | 0.020 | 4.1 |
| N-Benzyl-α-methylbenzylamine-R ||||||
| 1 | 0.369 | 0.388 | −0.019 | 0.019 | 4.9 |
| 2 | 0.847 | 0.835 | 0.012 | 0.012 | 1.4 |
| 3 | 0.306 | 0.294 | 0.012 | 0.012 | 4.1 |
| 4 | 9.65E−02 | 0.132 | −0.036 | 0.036 | 27 |
|  |  |  | Avg. | 0.020 | 9.3 |

Example 3

Generation and Evaluation of Regression Model for 1-2-Propanediol

Figure 10:
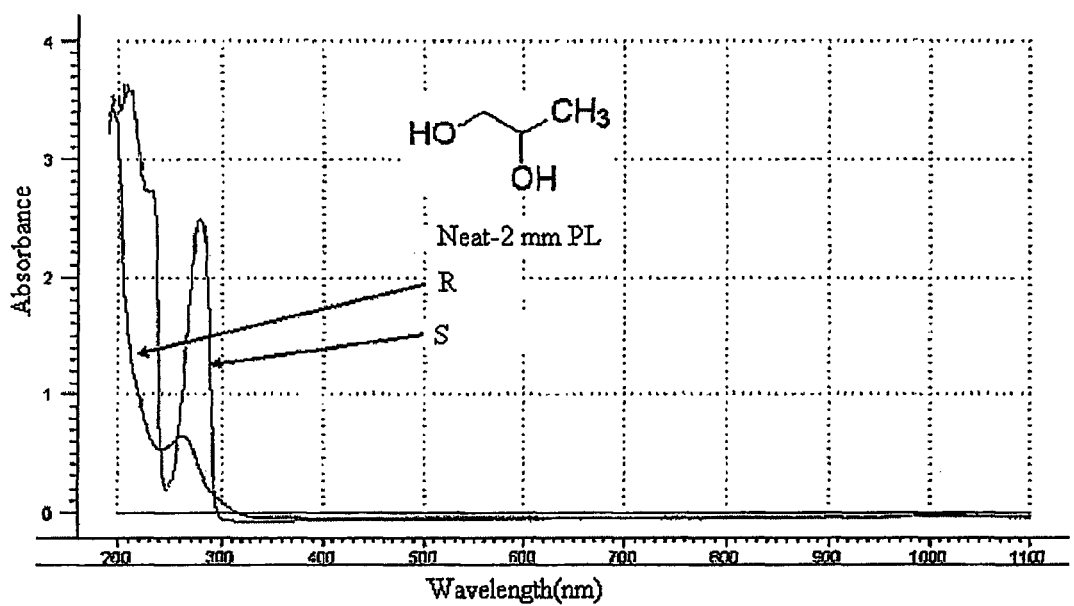
FIG. 10 shows the spectra of the R and S configurations of 1,2-propanediol taken neat with a quartz cell with a path length of 2 mm.
Figure 11:
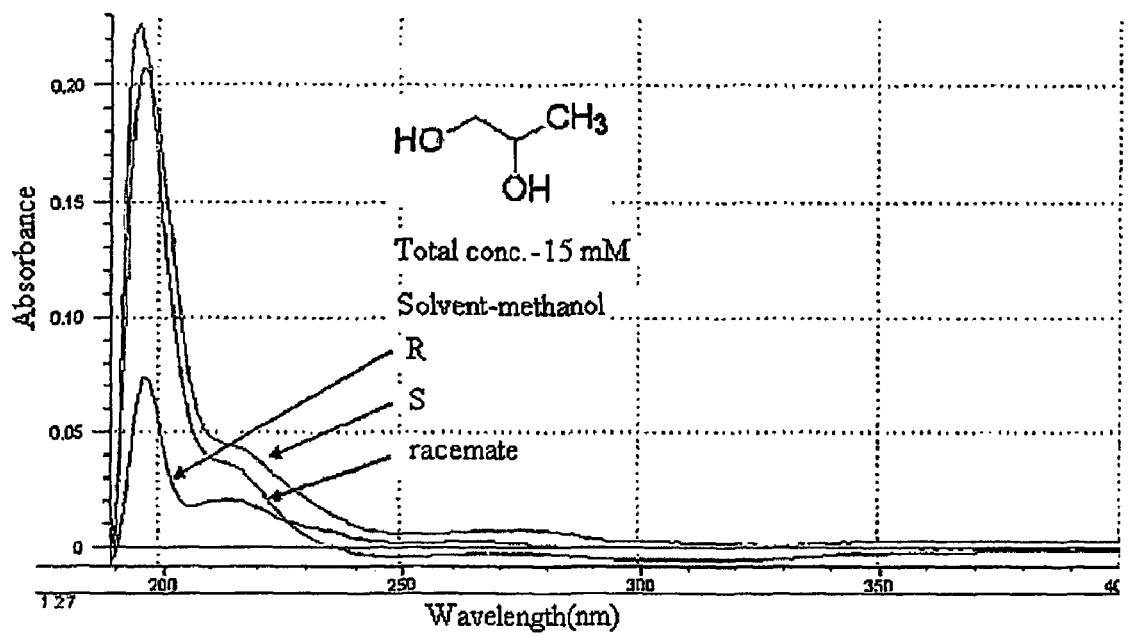
FIG. 11 shows three selected spectra from the calibration set of mixtures for 1,2-propanediol with a total concentration maintained at 15 mM with methanol as the solvent.

The compounds in this example were obtained from Aldrich (St. Louis, Mo.) and were used without further purification. In this case the spectra of the R and S configurations were markedly different even when taken neat as seen in FIG. 10. The absorption peaks are located in the same positions, but the envelopes of the bands and the intensities are quite different. In FIG. 11, the spectra of the diluted samples are seen in which the composition of one spectrum is 0 R-1 S, another is 1 R-0 S, and the racemic mixture is also shown. These are selected spectra from a calibration set containing eleven samples made in the same manner as for the other enantiomeric compounds. The total concentration was maintained at 15 mM, and the spectra were taken using a 2 mm path length quartz cell.

Figure 12:
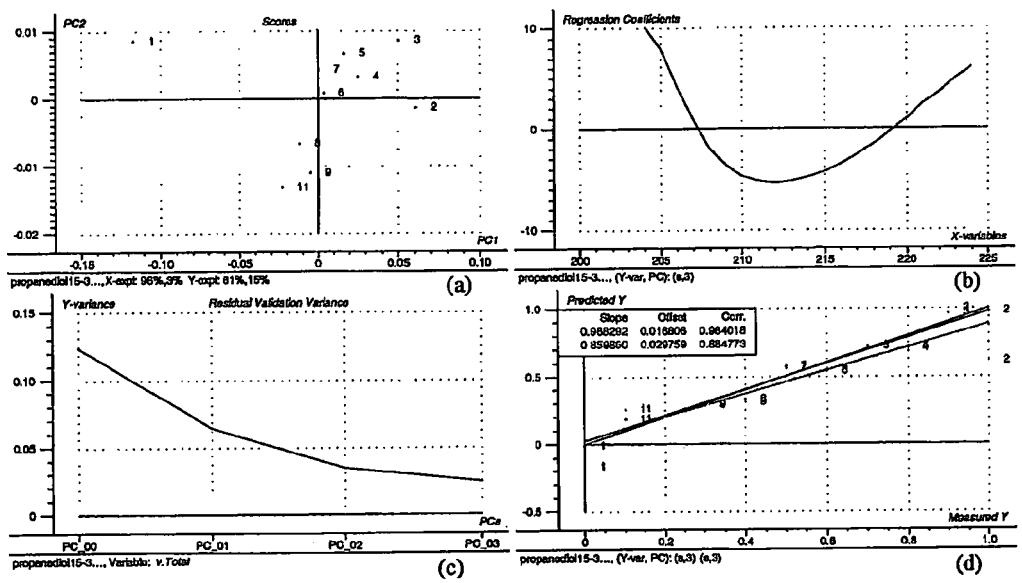
FIG. 12 shows the PLS1 regression model for (S) 1,2-propanediol solutions over a wavelength range of 205-225 nm: (a) Scores plot of the first principal component ("PC1") versus the second principal component ("PC2"); (b) Plot of the regression coefficients as a function of wavelength; (c) Residual variance as a function of the number of principal components; and (d) Plot of the concentration of (S) 1,2-propanediol predicted by the model versus the known value.

The spectral data were used to calculate a PLS1 regression model, which is shown in FIG. 12 for the S configuration. The wavelength range was 205-225 nm using three components. One sample was removed as an outlier. The correlation coefficient for the model was 0.98 with a validation coefficient of 0.88 as seen in FIG. 12(*d*). Two principal components explain 99 percent of the x variance and 96 percent of the y variance.

A validation set of solutions was also prepared and their spectra were taken. The regression model was used to predict the enantiomeric composition of the solutions. The results for the S configuration are presented in Table 3, with values reported as mole fractions. The average percent error for the predicted values was 6.5.

TABLE 3

Numeric results for prediction of the validation set of solutions
1,2-Propanediol-S
λ range 205-225

| Sample | Predict φ | Reference φ | Error | Abs. Error | % Error |
|---|---|---|---|---|---|
| 1 | 0.853 | 0.877 | −0.024 | 0.024 | 2.7 |
| 2 | 0.542 | 0.553 | −0.011 | 0.011 | 2.0 |
| 3 | 0.313 | 0.273 | 0.04 | 0.04 | 15 |
|  |  |  | Avg. |  | 6.5 |

Example 4

Generation and Evaluation of Regression Model for Limonene

Figure 13:
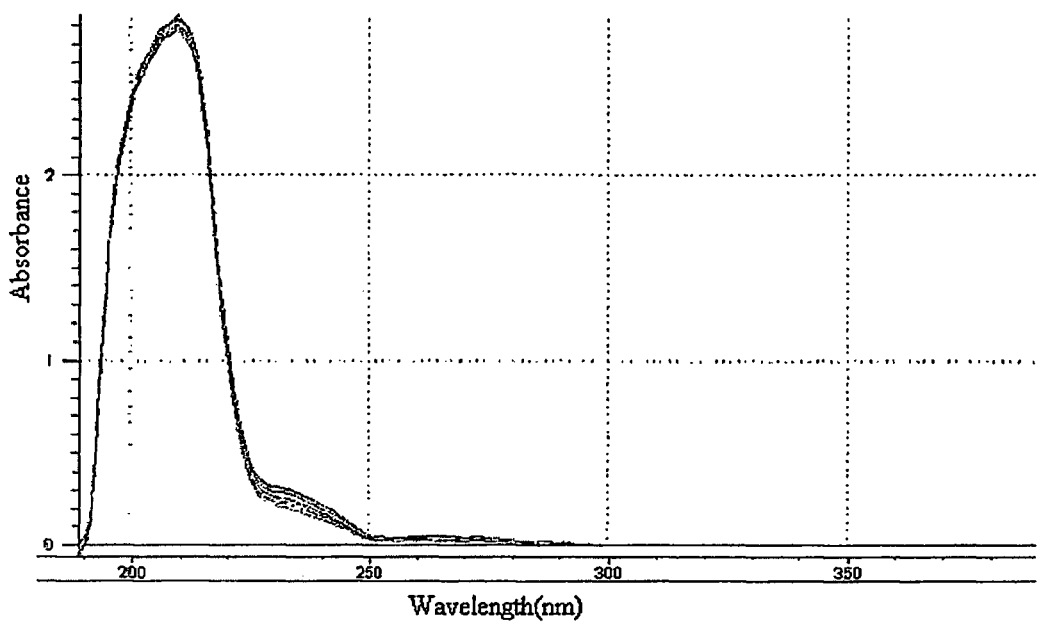
FIG. 13 shows the spectra of R and S limonene mixtures dissolved in methanol with a total concentration held constant at 1.5 mM.
Figure 14:
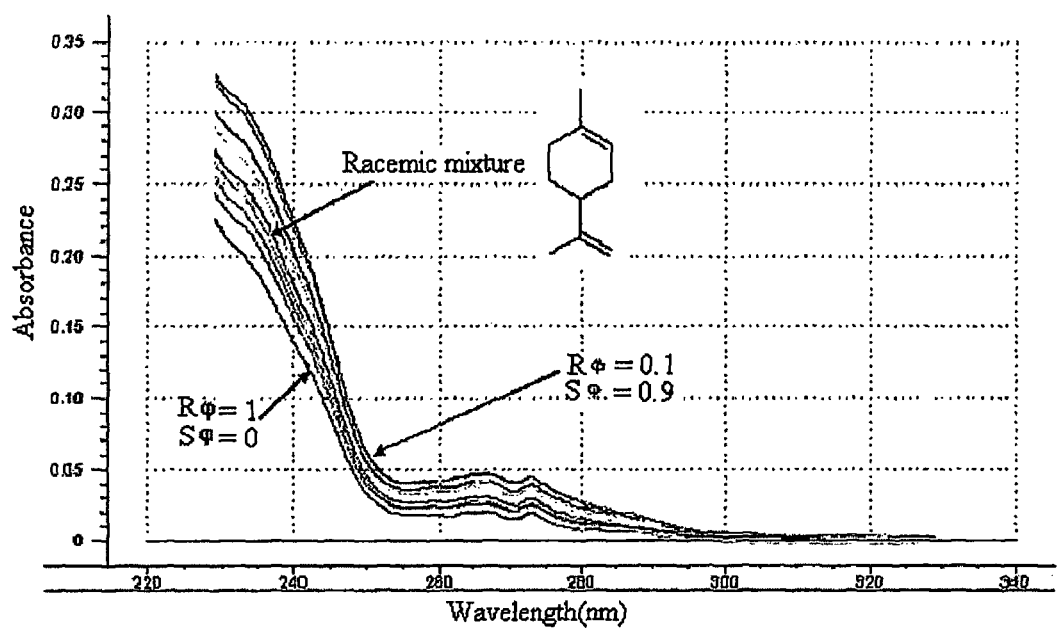
FIG. 14 shows the calibration set for limonene mixtures with methanol as the solvent.
Figure 15:
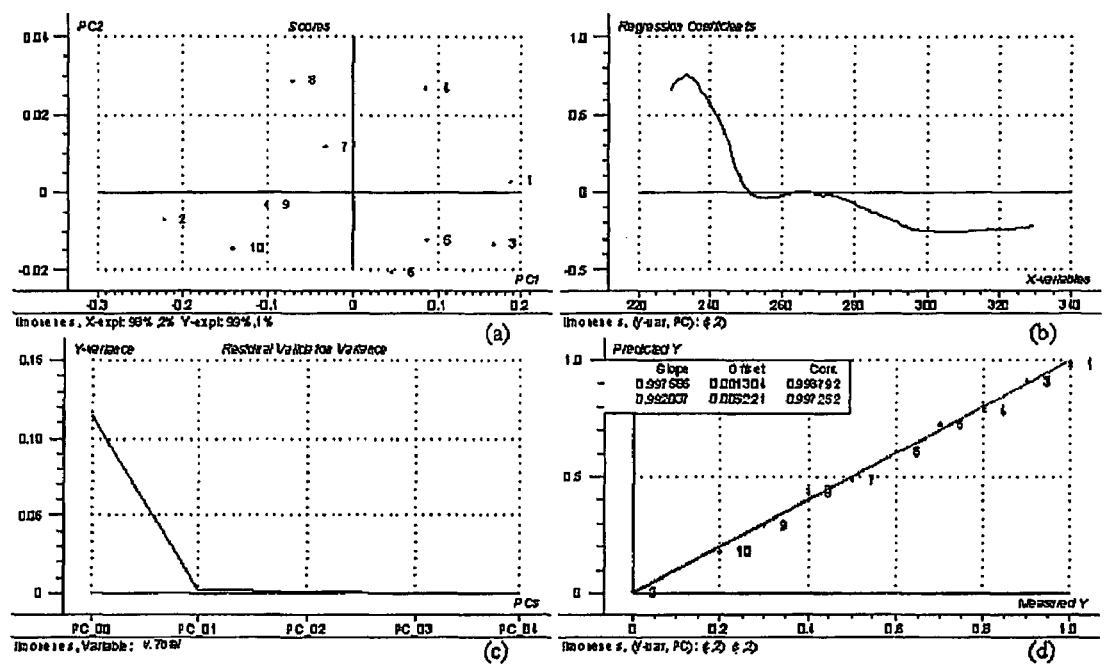
FIG. 15 shows the PLS1 regression model for (S) limonene solutions over a wavelength range of 230-330 nm: (a) Scores plot of the first principal component ("PC1") versus the second principal component ("PC2"); (b) Plot of the regression coefficients as a function of wavelength; (c) Residual variance as a function of the number of principal components; and (d) Plot of the concentration of (S) limonene predicted by the model versus the known value.
Figure 16:
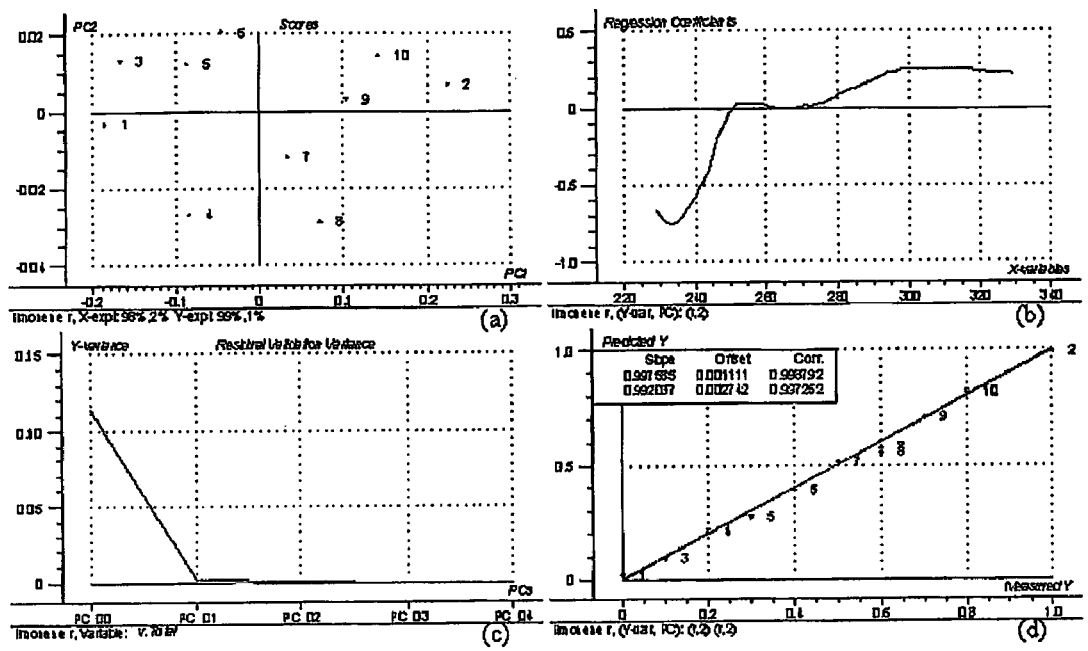
FIG. 16 shows the PLS1 regression model for (R) limonene solutions over a wavelength range of 230-330 nm: (a) Scores plot of the first principal component ("PC1") versus the second principal component ("PC2"); (b) Plot of the regression coefficients as a function of wavelength; (c) Residual variance as a function of the number of principal components; and (d) Plot of the concentration of (R) limonene predicted by the model versus the known value.

For limonene, as with the other enantiomeric pairs, a calibration set of solutions in methanol was prepared holding the total concentration at 15 mM. The mole fractions were varied from 0 R-1 S to 1 R-0 S in increments of 0.1 φ. FIG. 13 shows the spectra obtained with the calibration set and FIG. 14 shows the spectra with the wavelength scale set at the range used for the model. The spectrum for one of the solutions was not included since it was an outlier. The Unscrambler® software was used to calculate a PLS 1 model using the spectral data. The results are given in FIG. 15 for the S configuration and in FIG. 16 for the R-configuration.

For both the models the correlation and validation coefficients are greater than 0.99. An interesting point is the fact that the regression coefficient plots in frame (c) for the R and S forms are mirror images of themselves as in all the other compounds that were studied. The first two components of both models explain 100 percent of the x and y variance.

A validation set was then prepared using random compositions to be used to test the predictive ability of the model. Table 4 gives the numerical results of the predictions, with values reported as mole fractions. The absolute average deviation for both was 0.02 φ with an average percent error of 10% for the R configuration and 4% for the S enantiomer.

TABLE 4

Numerical results of the predictions for limonene R and S enantiomers

| Sample | Predicted | Reference | Error | Abs. Error | % Error |
|---|---|---|---|---|---|
| R-Limonene ||||||
| 1 | 0.46 | 0.48 | −0.02 | 0.02 | 4 |
| 2 | 0.81 | 0.78 | 0.03 | 0.03 | 4 |
| 3 | 0.43 | 0.44 | 0.00 | 0.00 | 0 |
| 4 | 0.16 | 0.12 | 0.03 | 0.03 | 30 |
|  |  |  | Avg. | 0.02 | 10 |
| S-Limonene ||||||
| 1 | 0.54 | 0.52 | 0.02 | 0.02 | 4 |
| 2 | 0.19 | 0.22 | −0.03 | 0.03 | 10 |
| 3 | 0.57 | 0.57 | 0 | 0 | 0 |
| 4 | 0.85 | 0.88 | −0.03 | 0.03 | 3 |
|  |  |  | Avg. | 0.02 | 4 |

Example 5

Generation of Regression Model for Limonene Using a Spectrometer Equipped with Polarizers Limonene with a specific rotation of $125_D^{20}$ was chosen as the enantiomeric compound for the analysis since it is relatively cheap and readily available. The specific rotation is large so this would be a test under ideal conditions for the technique. The rotation with a path length of 20 mm with neat mixtures will be approximately ±20 degrees. The calibration set was prepared using accepted volumetric techniques and consisted of eleven samples with mole fraction compositions ranging from 0 R-1 S to 1 R-0 S. A prediction set was also prepared to test the predictive performance of the model. Spectra were recorded with a Hewlett-Packard photodiode array (Model 8453) UV-visible spectrophotometer over the wavelength range from 190-1100 nm. A modified base holding two polarizers on either side of the sample cell holder was used in place of a standard cell holder. The second polarizer, closer to the diode array detector, was oriented 45 degrees relative to the first polarizer. The usable wavelength range of the polarizers is from 300 to 2500 nm. Multivariate regression was performed with a commercial chemometric software package (Unscrambler™ vers. 7.6, CAMO, Inc., Corvallis, Oreg.). Principal component analysis and partial least-squares regression were performed on the data using full cross-validation.

Figure 17:
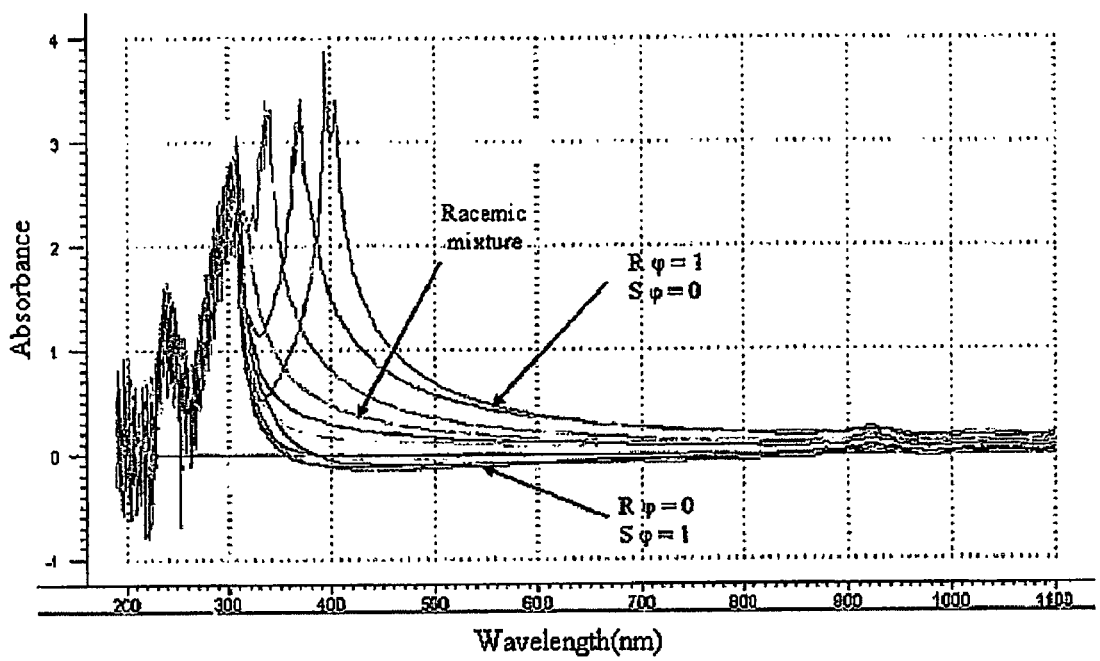
FIG. 17 shows the spectra over the wavelength range from 190-1100 nm for a calibration set of eleven different enantiomeric mixtures of R and S limonene, having mole fraction compositions ranging from 0 R-1 S to 1 R-0 S.
Figure 18:
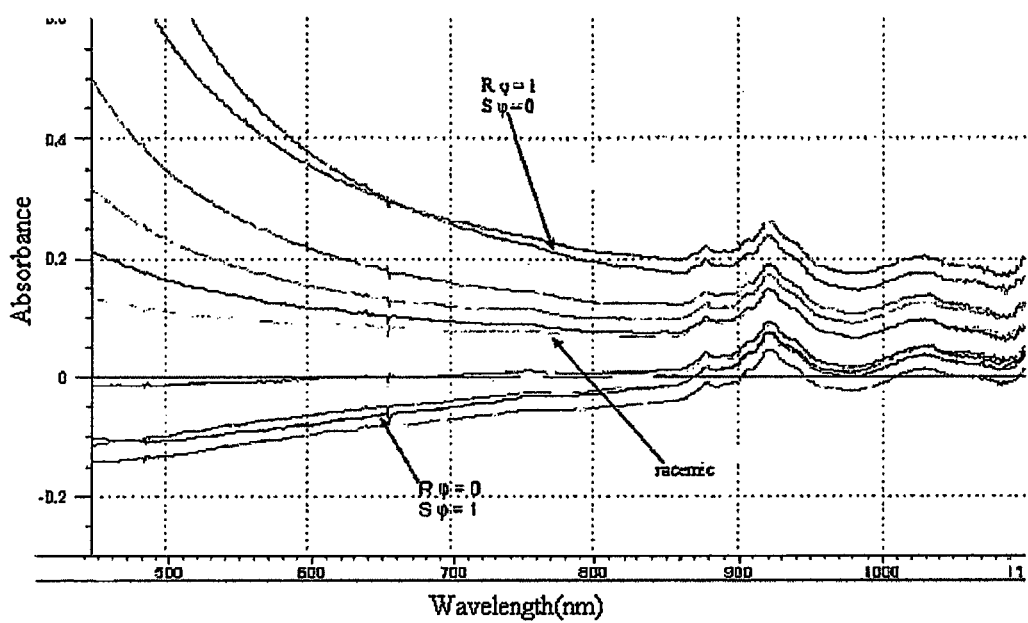
FIG. 18 shows the spectra of the same calibration set of eleven different enantiomeric mixtures of R and S limonene from FIG. 2, but over an adjusted wavelength range and absorbance scale.
Figure 19:
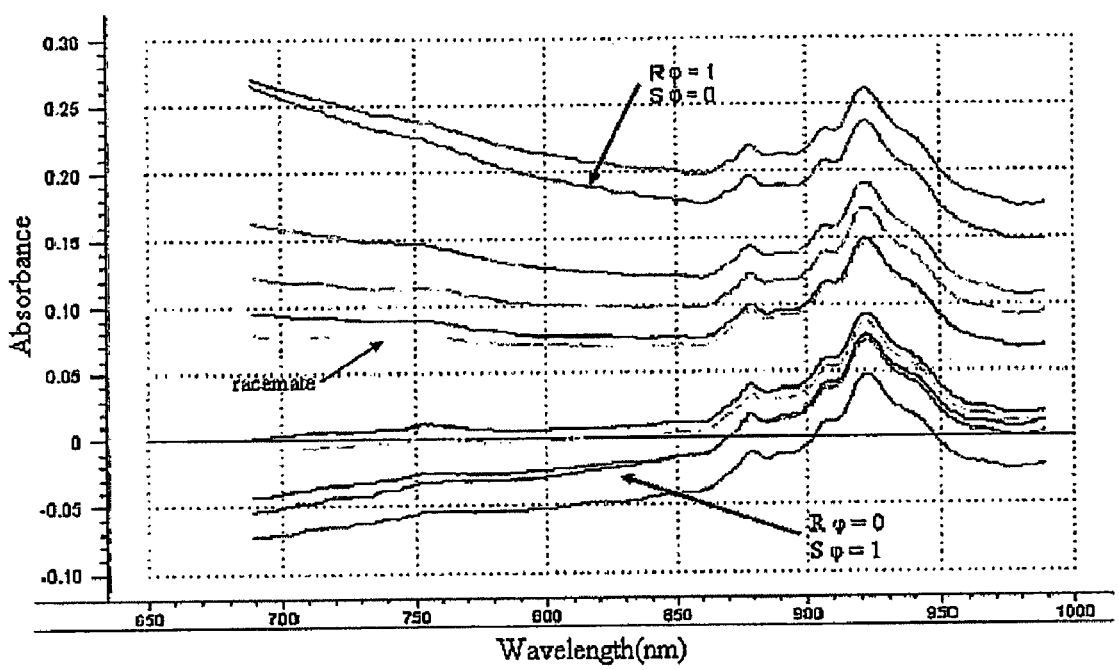
FIG. 19 shows the spectra of the same calibration set of eleven different enantiomeric mixtures of R and S limonene from FIGS. 2 and 3, but over the adjusted wavelength range of 690-990 nm used to calculate the regression models.

FIG. 17 shows the spectra of the samples in the calibration set of samples. It is apparent from the spectra that below about 450 nm most of the light is absorbed by the polarizers and/or absorption bands associated with limonene. A wavelength range above this cutoff level was chosen to calculate the model and make the predictions. FIG. 18 shows the same spectra using a different scale. FIG. 19 shows the spectra for the calibration set scaled to the final wavelength range (690-990 nm) used to calculate the models for prediction.

Figure 20:
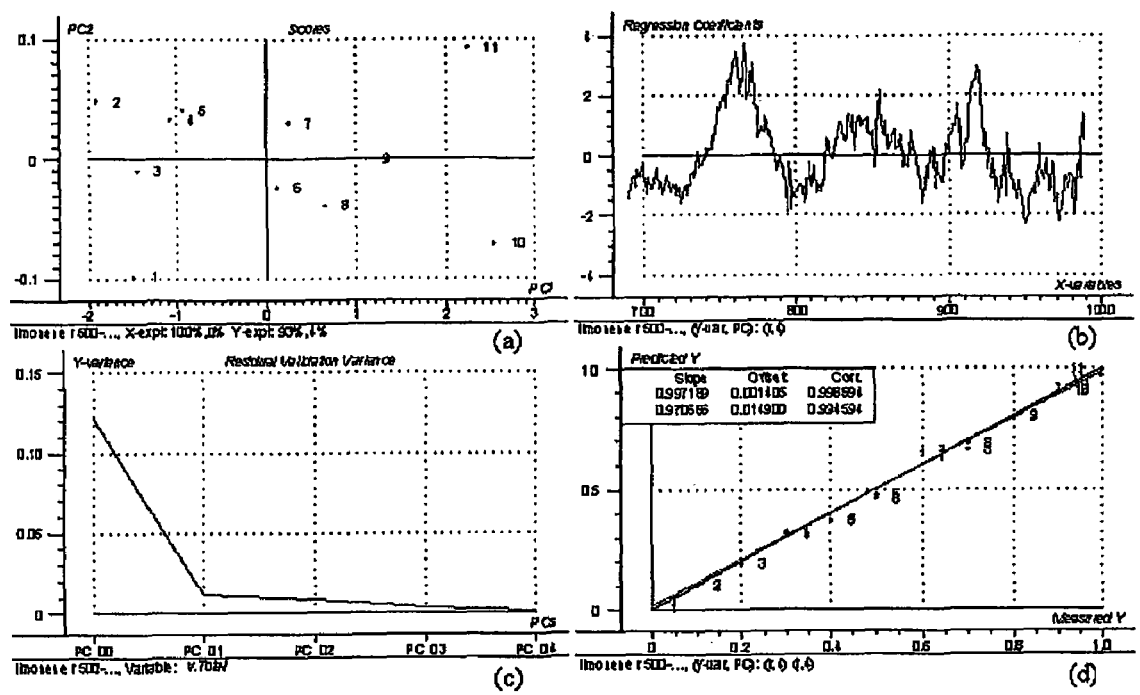
FIG. 20 shows a summary of the results for a PLS-1 regression of the spectral data over the wavelength range from 690-990 nm for R limonene with four principal components: (a) scores plot of the first principal component ("PC1") versus the second principal component ("PC2"); (b) regression coefficients as a function of wavelength; (c) residual variance as a function of the number of principal components; (d) plot of the concentration of R limonene predicted by the model versus the known values.

FIG. 20 shows the results for the PLS 1 model for the S-limonene configuration. The model explains with two principal components 100 percent of the x-variance and 97 percent of the y-variance. The predicted vs. measured plot in frame (d) of FIG. 5 indicates a correlation coefficient of 0.998 and a validation coefficient of 0.994.

Example 6

Prediction of Enantiomeric Composition of Limonene Using Regression Model

The prediction set of samples of limonene having known enantiomeric compositions was then measured to test the predictive ability of the model. The results are shown in Table 5 below. Values reported are mole fractions.

TABLE 5

Numerical results for the prediction of R and S limonene mixtures

S-Limonene (690-990 nm)

| Sample | Predicted | Reference | Error | Abs. Error | % Error | % Error[a] |
|---|---|---|---|---|---|---|
| 12 | 0.62 | 0.88 | −0.26 | 0.26 | 30 | 30 |
| 13 | 0.25 | 0.25 | 0 | 0 | 0 | 0 |
| 14 | 0.47 | 0.55 | −0.08 | 0.08 | 15 | 20 |
| 15 | 0.74 | 0.75 | −0.01 | 0.01 | 1 | 1 |
| 16 | 0.1 | 0.12 | −0.02 | 0.02 | 17 | 20 |
|  |  |  | Avg. | 0.07 | 13 | 14 |

R-Limonene (690-990 nm)

| Sample | Predicted | Reference | Error | Abs. Error | % Error | % Error[a] | Error[b] |
|---|---|---|---|---|---|---|---|
| 12 | 0.38 | 0.12 | 0.26 | 0.26 | 217 | 200 |  |
| 13 | 0.75 | 0.75 | 0 | 0 | 0 | 0 | 0 |
| 14 | 0.53 | 0.45 | 0.08 | 0.08 | 18 | 20 | 20 |
| 15 | 0.27 | 0.25 | 0.02 | 0.02 | 8 | 8 | 8 |
| 16 | 0.9 | 0.88 | 0.02 | 0.02 | 2 | 2 | 2 |
|  |  |  | Avg. | 0.07 | 49 | 46 | 8 |

[a] % Error corrected for sig. fig.
[b] Avg. % error calculated without high % error sample.

The average percent error for predicting the S enantiomer was 14% while the percent error for the R enantiomer was high at more than 40 percent. However, the prediction for the lowest mole fraction was the source of most of the error. When this value was removed from the prediction set the percent error for the R enantiomer was lowered to 8%.

What is claimed is:

1. A method for determining an unknown enantiomeric composition of a chiral compound in an unknown sample, comprising:
   preparing a series of known samples, each of the known samples comprising a chiral compound having a known enantiomeric composition, wherein, in each of the known samples, the enantiomeric composition of the chiral compound is varied;
   collecting pseudo-absorption spectral data of the known samples by passing light of various wavelengths through a first polarizer, the known sample, and a second polarizer oriented at a 45 degree angle with respect to the first polarizer, and recording the resultant light intensity with a spectrometer;
   performing a principal component analysis to select a spectral range of wavelengths in which the spectral differences arising in each of the known samples due to an influence of the enantiomeric composition is most appreciable to give the selected range of wavelengths;
   performing a partial-least-squares regression of the spectral data over the selected range of wavelengths for each of the series of the known samples to determine a series of regression coefficients and a regression constant;

entering the series of regression coefficients for the selected range of wavelengths into a regression vector;

collecting "pseudo-absorption" spectral data of an unknown sample by passing light of various wavelengths through a first polarizer, the unknown sample, and a second polarizer oriented at a 45 degree angle with respect to the first polarizer, and recording the resultant light intensity with a spectrometer to give unknown spectral data, wherein the unknown sample comprises the chiral compound of the known samples having an unknown enantiomeric composition; and inserting the unknown spectral data into the regression vector to allow calculation of the unknown enantiomeric composition of the chiral compound in the unknown sample.

2. The method of claim 1, wherein the regression vector is:

$X_R = k_0 + k_1 A_1 + k_2 A_2 + \ldots + k_n A_n,$ and wherein:

$X_R$ is the unknown enantiomeric composition of the chiral compound in the unknown sample, $k_i$ is the series of regression coefficients calculated for each of the wavelengths in the selected range of wavelengths, $A_i$ is the pseudo-absorption spectral data of the unknown compound at each of the wavelengths in the selected range of wavelengths, i is the selected range of wavelengths, 1-n, and $k_0$ is the regression constant.

3. The method of claim 1, wherein the chiral compound is any chiral compound capable of rotating the plane of oscillation of a linearly polarized light beam.

4. The method of claim 1, wherein the chiral compound is limonene.

* * * * *